United States Patent
Yang et al.

(10) Patent No.: US 10,094,831 B2
(45) Date of Patent: Oct. 9, 2018

(54) NOROVIRUS DETECTION SENSOR AND ELECTROCHEMICAL SENSING METHOD USING THE SAME

(71) Applicants: GWANGJU INSTITUTE OF SCIENCE AND TECHNOLOGY, Gwangju (KR); KOREA BASIC SCIENCE INSTITUTE, Daejeon (KR); INDUSTRY FOUNDATION OF CHONNAM NATIONAL UNIVERSITY, Gwangju (KR)

(72) Inventors: Sung Yang, Gwangju (KR); Du-Woon Kim, Gwangju (KR); Joseph Kwon, Daejeon (KR); Sung-A Hong, Gwangju (KR); Jong-Soon Choi, Daejeon (KR); Heemin Lee, Gwangju (KR)

(73) Assignees: GWANGJU INSTITUTE OF SCIENCE AND TECHNOLOGY, Gwangju (KR); KOREA BASIC SCIENCE INSTITUTE, Daejeon (KR); INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 14/584,394

(22) Filed: Dec. 29, 2014

(65) Prior Publication Data

US 2016/0061834 A1 Mar. 3, 2016

(30) Foreign Application Priority Data

Sep. 2, 2014 (KR) ........................ 10-2014-0116199

(51) Int. Cl.
*G01N 33/569* (2006.01)
*G01N 27/327* (2006.01)
*G01N 33/543* (2006.01)

(52) U.S. Cl.
CPC ... *G01N 33/56983* (2013.01); *G01N 27/3276* (2013.01); *G01N 33/5438* (2013.01); *G01N 2333/08* (2013.01)

(58) Field of Classification Search
CPC ......... G01N 33/56983; G01N 33/5438; G01N 27/3276
See application file for complete search history.

(56) References Cited

U.S. PATENT DOCUMENTS

2002/0179439 A1* 12/2002 Weng .................. B01J 19/0046
506/21
2004/0100893 A1* 5/2004 Germishuizen ........ B82Y 10/00
369/108

(Continued)

OTHER PUBLICATIONS

(Supportive Materials on Jul. 30, 2014) Sung A Hong et al., Selective, sensitive and electrochemical detection of norovirus using alternative protein, Jul. 30, 2014, 3 pages, ISMM conference.

*Primary Examiner* — Melanie Yu Brown
(74) *Attorney, Agent, or Firm* — Hauptman Ham, LLP (57) ABSTRACT

Disclosed herein are a norovirus detection sensor and an electrochemical sensing method using the sensor. Specifically, in the norovirus detection sensor including a bioreceptor and a signal detector, a three-dimensional gold nanosurface electrode is used as a substrate, and the bioreceptor employs concanavalin A as a sample capture agent immobilized to the substrate and capable of binding to norovirus. Therefore, the norovirus detection sensor has improved sensitivity by employing the three-dimensional gold nanosurface electrode having a wide surface area. In addition, the norovirus detection sensor has effects of reducing manufacturing costs using a non-antibody material, i.e., concanavalin A which is inexpensive and readily available.

2 Claims, 11 Drawing Sheets

(56) References Cited

U.S. PATENT DOCUMENTS

2005/0208592 A1* 9/2005 Caron .............. G01N 33/54373
 435/7.1
2011/0312518 A1* 12/2011 Davis ................ B01L 3/502761
 506/9
2014/0087375 A1* 3/2014 Kelley ................. C12Q 1/6816
 435/6.11

* cited by examiner

NOROVIRUS DETECTION SENSOR AND ELECTROCHEMICAL SENSING METHOD USING THE SAME

CROSS REFERENCE TO RELATED APPLICATION

This application claims the benefit of Korean Patent Application No. 10-2014-0116199, filed on Sep. 2, 2014, entitled "NOROVIRUS DETECTION SENSOR AND ELECTROCHEMICAL SENSING METHOD USING THE SAME", which is hereby incorporated by reference in its entirety into this application.

BACKGROUND

1. Technical Field

The present invention relates to a biosensor, and more particularly, to a norovirus detection sensor and an electrochemical sensing method using the same.

2. Description of the Related Art

A biosensor is a biological analysis device for sensing a state and concentration of a target material based on characteristics of organisms, such as cells or tissues of animals and plants, enzymes, microorganisms, and the like. A biosensor typically includes a bioreceptor that senses and receives a target material, and a transducer that converts the sensed target material into a physically measurable signal. Such a biosensor is widely used in medicine for the purpose of analyzing bio-samples, such as blood, tissue cells, and the like. Recently, with growing interest in consumer health and wellbeing, use of biosensors is gradually broadened to foods analysis, environmental science, and so on.

On the other hand, noroviruses are food and water-mediated pathogenic microorganisms. When noroviruses are transmitted by food or water, the viruses cause infectious gastroenteritis in humans and thus are known as one of enteric viruses. Specifically, noroviruses are RNA viruses belonging to family Caliciviridae and genetically classified into five genogroups (GI-GV). Thereamong, it is known that human norovirus infection is mostly caused by eight genotypes of genogroup GI and 17 genotypes of genogroup GII. Exposure to only 100 particles of norovirus can cause symptoms such as diarrhea, stomach pain, vomiting, and the like. Vomit or feces excreted by such symptoms contain about one hundred million norovirus particles, which have strong infectivity and rapid transmission speed. In this regard, there is strong demand for technologies for detection and prevention of norovirus existing in food or water. In order to detect such noroviruses, sensor devices for sensing real-time polymerase chain reaction using nucleic acid-based techniques have been mostly employed. The real-time polymerase chain reaction uses norovirus RNA as a template and amplifies genetic information using polymerase, thereby selectively and specifically detecting norovirus based on the amplified genetic information.

However, such typical technologies using nucleic acids have drawbacks in that the technologies require various and complicated sample pre-treatment techniques, which consume much time and are expensive. Further, it is difficult to make a compact sensor device due to use of expensive specialized equipment. In addition, there is a restriction in detection of norovirus present at low concentration in contaminated foods.

BRIEF SUMMARY

The present invention has been conceived to solve the problems in the art and embodiments of the present invention provide a sensor capable of reducing detection time and cost for manufacturing sensor devices while securing high sensitivity and high selectivity, and a sensing method using the sensor.

One aspect of the present invention provides a norovirus detection sensor, which includes: a biological sample receptor (hereinafter referred to as "bioreceptor") and a signal detector, wherein a three-dimensional gold nanosurface electrode is used as a substrate and the bioreceptor employs concanavalin A as a sample capture agent immobilized to the substrate and capable of binding to norovirus.

The three-dimensional gold nanosurface electrode may be formed through an electrochemical deposition process.

The substrate to which concanavalin A is immobilized may further include mercaptohexanol.

The signal detector may detect electrochemical signals generated from the bioreceptor and qualitatively and quantitatively calculate measured values of biological samples.

Another aspect of the present invention provides an electrochemical sensing method using a norovirus detection sensor including a bioreceptor and a signal detector. The method includes: combining a norovirus sample with concanavalin A as a capture agent capable of binding to norovirus and immobilized to a three-dimensional gold nanosurface electrode of the bioreceptor to form a conjugate; labeling the resulting conjugate with an antibody for labeling detection signals (hereinafter referred to as "detection antibody"); generating an electrochemical signal by the detection antibody; and measuring the electrochemical signal using the signal detector.

The labeling the resulting conjugate with a detection antibody may be performed successively using a primary antibody selectively binding to norovirus included in the conjugate and a secondary antibody to which an electrochemical enzyme is linked.

Electrochemical signals may occur by the antibody labeled on the conjugate and the electrochemical enzyme linked to the secondary antibody.

The electrochemical sensing method using the norovirus detection sensor may have limit of detection (LOD) ranging from 35 copies/mL to 60 copies/mL.

The electrochemical sensing method using the norovirus detection sensor may have a detection selectivity for norovirus of 98% or more.

A further aspect of the present invention provides an electrochemical sensing method using a norovirus detection sensor including a bioreceptor and a signal detector. The method includes: combining a norovirus sample including a ferricyanide solution with concanavalin A as a capture agent capable of binding to norovirus immobilized to a three-dimensional gold nanosurface electrode of the bioreceptor; and measuring electrochemical signals generated by oxidation and reduction (hereinafter referred to as "redox reaction") of the ferricyanide solution using the signal detector. The intensity of the electrochemical signals generated by redox reaction of the ferricyanide solution may depend on a concentration of the norovirus sample.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Hereinafter, various embodiments of the present invention will be described in detail in reference to the accompanying drawings.

The present invention can be modified and varied in various ways, and some specific embodiments are provided for illustration in the drawings and will be described in detail below. However, it should be understood that the present invention is not limited to specific embodiments and that various modifications can be made by those skilled in the art without departing from the scope of the present invention defined by the appended claims and equivalents thereof.

It should be understood that the drawings are not to precise scale and may be exaggerated or scaled down in thickness of layers and regions for clarity. Like components will be denoted by like reference numerals throughout the specification.

One aspect of the present invention provides a norovirus detection sensor. Specifically, the norovirus detection sensor may include a bioreceptor and a signal detector, wherein a three-dimensional gold nanosurface electrode is used as a substrate, and the bioreceptor employs concanavalin A as a sample capture agent immobilized to the substrate and capable of binding to norovirus.

Specifically, the bioreceptor included in the norovirus detection sensor may refer to a device capable of sensing, immobilizing or capturing biological samples as target substances to be measured and detected. In the present invention, the biological samples as target substances may include norovirus as a target substance to be detected. The bioreceptor may employ concanavalin A as a capture agent capable of binding to norovirus in order to allow norovirus to be immobilized to the three-dimensional gold nanosurface electrode used as the substrate.

Specifically, the signal detector included in the norovirus detection sensor may sense electrochemical signals generated from the bioreceptor and qualitatively and quantitatively calculate measured values of biological samples. When a biological sample as a target substance is supplied to the bioreceptor, the signal detector may sense electrochemical signals generated either by labeling the bioreceptor with a specific antibody capable of generating electrochemical signals or by further adding a substance capable of generating electrochemical signals without labeling (i.e., label-free), and represents qualitatively and quantitatively measured values such as constituents, presence or absence and concentrations of the biological samples.

Figure 1:
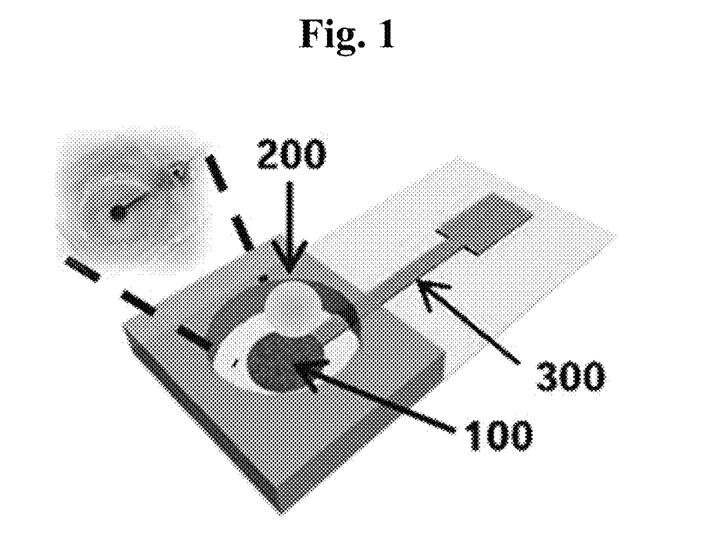
FIG. 1 is a schematic view of a norovirus detection sensor in accordance with one embodiment of the present invention.

FIG. 1 is a schematic view of a norovirus detection sensor in accordance with one embodiment of the present invention.

Referring to FIG. 1, the norovirus detection sensor may be configured to bring a biological sample as a target substance to be measured and detected, namely, a norovirus containing sample, into contact with a bioreceptor 100 on which a substrate having a capture agent capable of capturing a biological sample is disposed. In addition, the norovirus detection sensor may be provided with a signal detector 300 that is electrochemically connected to the bioreceptor 100 and capable of sensing and detecting an electrochemical signal generated when the bioreceptor 100 contacts norovirus 200.

The bioreceptor according to the present invention will be described in detail with reference to FIGS. 2 to 4. However, it should be understood that FIGS. 2 to 4 show merely illustrative examples and the present invention is not limited thereto.

Figure 2:
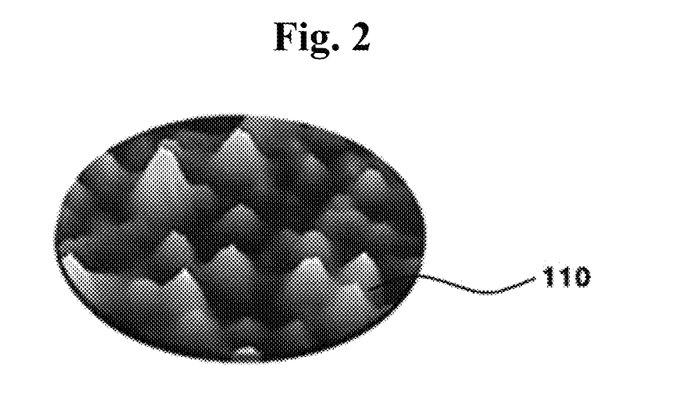
FIG. 2 is a schematic view of a bioreceptor in accordance with one embodiment of the present invention.
Figure 3:
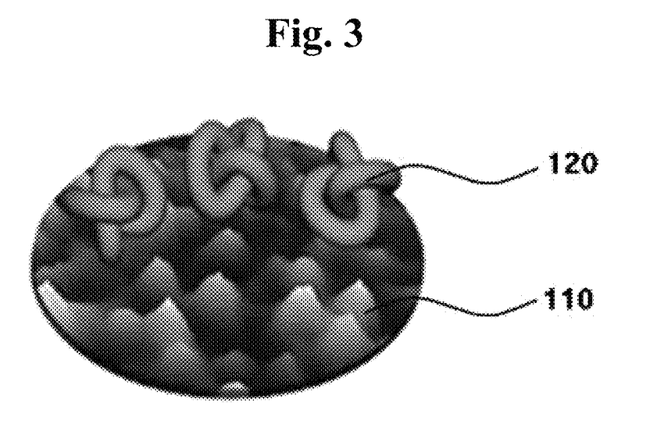
FIG. 3 is a schematic view of the bioreceptor in accordance with the embodiment of the present invention.
Figure 4:
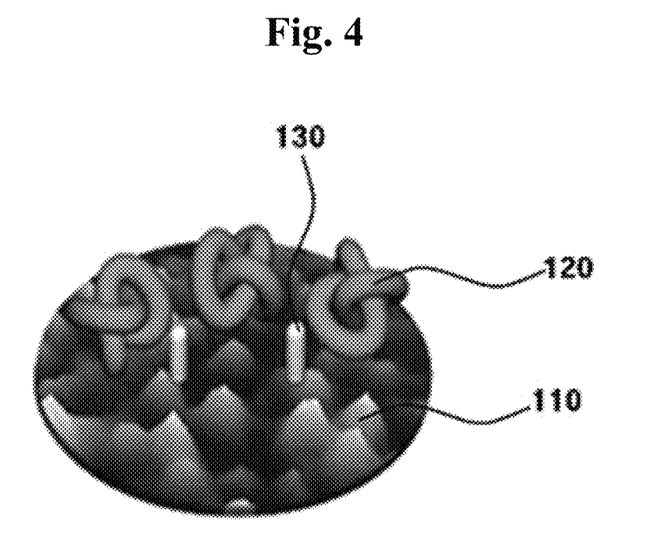
FIG. 4 is a schematic view of the bioreceptor in accordance with the embodiment of the present invention.

FIGS. 2 to 4 are schematic views of a bioreceptor in accordance with one embodiment of the present invention.

Referring to FIG. 2, a substrate 110 may be a three-dimensional gold nanosurface electrode. Specifically, the three-dimensional gold nanosurface electrode may be formed through electrochemical deposition. More specifically, a gold (Au) thin layer serving as a seed for forming a structure having a three-dimensional gold nanosurface is formed on the substrate 110. Through electrochemical deposition on the gold thin layer, gold particles may be deposited on the gold thin layer, thereby forming gold crystals. The gold crystals grown by deposition of the gold particles on the gold thin layer may form a three-dimensional nanosurface structure as the gold particles pass through deposition growth in all-directions. Such a three-dimensional nanosurface structure may have increased surface area due to structural characteristics thereof. Accordingly, when the three-dimensional gold nanosurface electrode is used as the substrate 110 for the sensor, the sensor may have improved sensitivity and selectivity. Namely, the norovirus detection sensor according to the present invention employing the three-dimensional gold nanosurface electrode may have properties of high sensitivity and high selectivity.

As shown in FIG. 3, it is possible to immobilize concanavalin A 120 on the three-dimensional gold nanosurface electrode used as the substrate 110. Concanavalin A 120 is a non-antibody material, and can selectively bind norovirus as the target substance. Concanavalin A 120 is a crystalline protein obtained from seeds of *Canavalia ensiformis*, and has biological properties of high binding affinity to specific saccharides. The present invention employs such a saccharide specific binding property of concanavalin A 120. When the bioreceptor contacts a norovirus sample, norovirus is attached to concanavalin A 120, thereby capturing norovirus at the bioreceptor.

In addition, mercaptohexanol 130 may be further added to the substrate 110 to which concanavalin A 120 is immobilized. Specifically, after concanavalin A 120 is immobilized on the substrate 110 provided as the three-dimensional gold nanosurface electrode, mercaptohexanol 130 may be further added to an exposed area of the three-dimensional gold nanosurface electrode, in which concanavalin A 120 is not formed on the substrate 110, to fill the exposed area of the substrate 110 therewith, as depicted in FIG. 4. As such, mercaptohexanol 130 may serve to block the exposed area of the substrate 130 in which concanavalin A 120 is not formed on the substrate 110 and prevent other materials from non-specifically binding to the substrate 110. Milk protein or bovine serum albumin (BSA) and the like may be used instead of mercaptohexanol depending upon embodiments.

As described above, the norovirus detection sensor according to the present invention employs a three-dimensional gold nanosurface electrode having a wide surface area as the substrate to improve sensitivity of the sensor, thereby enabling detection with high sensitivity. In addition, the norovirus detection sensor according to the present invention employs concanavalin A which is an inexpensive and readily available non-antibody material as a biological sample capture agent, thereby reducing manufacturing costs.

Another aspect of the present invention provides an electrochemical sensing method using the norovirus detection sensor. Specifically, the electrochemical sensing method employs the norovirus detection sensor including a bioreceptor and a signal detector, and may include: 1-1) combining a norovirus sample with concanavalin A as a capture agent capable of binding to norovirus and immobilized to a three-dimensional gold nanosurface electrode of the bioreceptor to form a conjugate; 1-2) labeling the resulting conjugate with a detection antibody; 1-3) generating an electrochemical signal by the detection antibody; and 1-4) measuring the electrochemical signal using the signal detector.

In step 1-1), a norovirus sample is bound to concanavalin A as a capture agent which is immobilized to the three-dimensional gold nanosurface electrode of the bioreceptor and capable of binding to norovirus.

The bioreceptor included in the norovirus detection sensor may, as described in one aspect of the present invention, employ a three-dimensional gold nanosurface electrode as a substrate, to which concanavalin A as a capture agent capable of capturing norovirus and capable of binding to norovirus is immobilized. Additionally, mercaptohexanol may be applied together with concanavalin A to the substrate.

When the bioreceptor is brought into contact with a norovirus sample, concanavalin A acting as a capture agent immobilized to the bioreceptor captures norovirus such that norovirus is immobilized to the bioreceptor. Namely, concanavalin A of the bioreceptor and the norovirus sample are bound to form a conjugate.

In step 1-2), the resulting conjugate is labeled with a detection antibody.

In order to detect norovirus captured at the bioreceptor by concanavalin A, a detection antibody capable of detecting norovirus may be used. Herein, the term "detection" may be quantitative measurement representing concentrations of norovirus in the norovirus sample, or qualitative measurement capable of specifically separating or differentiating norovirus from other microorganisms depending upon embodiments.

The detection antibody refers to an antibody capable of selectively binding to norovirus. Any known antibodies against norovirus may be used as the detection antibody without limitation. This is because norovirus antibodies from animals or humans are very non-specific in that the norovirus antibodies exhibit different immunological resistance and will bind to many genotypes of norovirus.

According to embodiments, the detection antibody may be classified into a primary antibody and a secondary antibody, which are successively used. Specifically, in one embodiment of the invention, the step of labeling the conjugate with the detection antibody may be performed using a primary antibody capable of selectively binding to norovirus of the conjugate and then a secondary antibody to which an electrochemical enzyme is linked.

The primary antibody refers to an antibody capable of selectively binding to norovirus to form an antigen-antibody conjugate with norovirus. When the primary antibody contacts the conjugate, norovirus in the conjugate and the primary antibody may form an antigen-antibody conjugate. Then, the primary antibody bound to norovirus may be labeled with the secondary antibody which recognizes the primary antibody as an antigen, wherein an electrochemical enzyme may be linked to the secondary antibody.

The electrochemical enzyme linked to the secondary antibody may be linked to the secondary antibody to electrochemically label the conjugate having no redox function.

In step 1-3), an electrochemical signal may be generated by the detection antibody.

Specifically, the electrochemical enzyme having high specificity for a substrate is linked to the secondary antibody, which finally leads to labeling of norovirus included in the conjugate, thereby measuring the degree of generation of the electrochemical signal by the electrochemical enzyme capable of serving as an electrochemical catalyst, which in turn allows qualitative and quantitative detection and measurement of norovirus. Specifically, a substance for electrochemical detection capable of inducing electrochemical reaction may be introduced by the electrochemical enzyme. The electrochemical enzyme can participate in redox reaction of the substance for the electrochemical detection introduced upon signal measuring using the signal detector, thereby generating electrons through oxidation of the substance for electrochemical detection. Accordingly, the signal detector can measure the concentration of norovirus captured at the bioreceptor by measuring the amount of electrons generated by the electrochemical enzyme.

Examples of the electrochemical enzyme may include HRP (horseradish peroxidase), ALP (alkaline phosphatase), or β-galactosidase, without being limited thereto. Since the electrochemical enzyme may have different degrees of activation depending upon pH, detection efficiency may be enhanced by adjusting pH by which activation may be optimized depending upon enzymes used.

In one embodiment of the invention, when an aqueous solution including 4-aminophenyl phosphate (APP) is used as the electrochemical measuring solution, redox reaction may be generated by the electrochemical enzyme, as shown in Reaction Formula 1.

[Reaction Formula 1]

4-aminophenyl phosphate (APP)

4-aminophenol (AP)

4-quinoneimine (QI)

Specifically, in order to measure the concentration of norovirus captured at the bioreceptor labeled with the primary antibody and the secondary antibody to which the electrochemical enzyme is linked, when a substance for electrochemical measurement including APP (4-aminophenyl phosphate) is supplied, APP is oxidized by the electrochemical enzyme linked to the secondary antibody, thereby forming AP (4-aminophenol) as shown in Reaction Formula 1, which in turn is oxidized again at 0.1V to form QI (4-quinoneimine), thereby generating electrons. In summary, the substance for electrochemical measurement is oxidized by the electrochemical enzyme to generate electrons, whereby the concentration of norovirus labeled with the secondary antibody to which the electrochemical enzyme is linked can be measured through measurement of the amount of electron generated by oxidation of the substance.

According to embodiments, the solution for electrochemical measurement may include ascorbic acid 2-phosphate (AAP), 1-naphthyl phosphate (NPP), 4-amino-1-naphthyl phosphate (ANP), and the like.

In step 1-4), the electrochemical signal is detected using the signal detector. Specifically, the electrochemical signal generated by the detection antibody, namely, by electrochemical enzyme linked to the detection antibody in step 1-3) may be converted into a physically measured value to calculate the measured value using the signal detector. As an electrochemical signal converter, any device well-known in the art may be used.

The electrochemical sensing method using a detection antibody according to the present invention will be described in detail with reference to FIGS. 5 to 7. However, it should be understood that FIGS. 5 to 7 show only illustrative examples and the present invention is not limited thereto.

Figure 5:
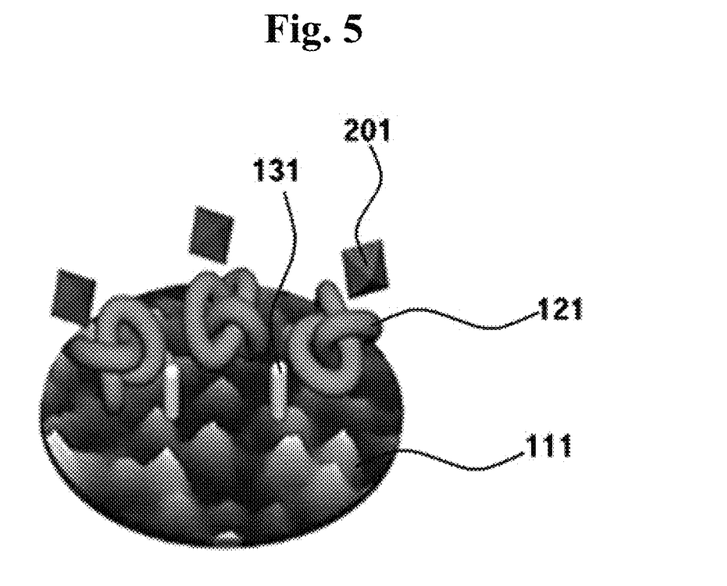
FIG. 5 is a schematic view illustrating an electrochemical sensing method using a norovirus detection sensor in accordance with one embodiment of the present invention.
Figure 6:
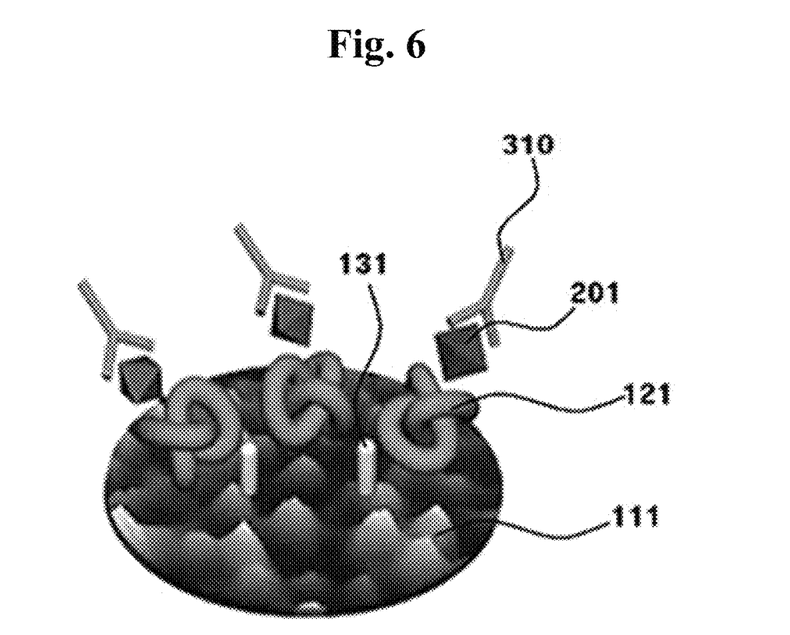
FIG. 6 is a schematic view illustrating the electrochemical sensing method using a norovirus detection sensor in accordance with the embodiment of the present invention.
Figure 7:
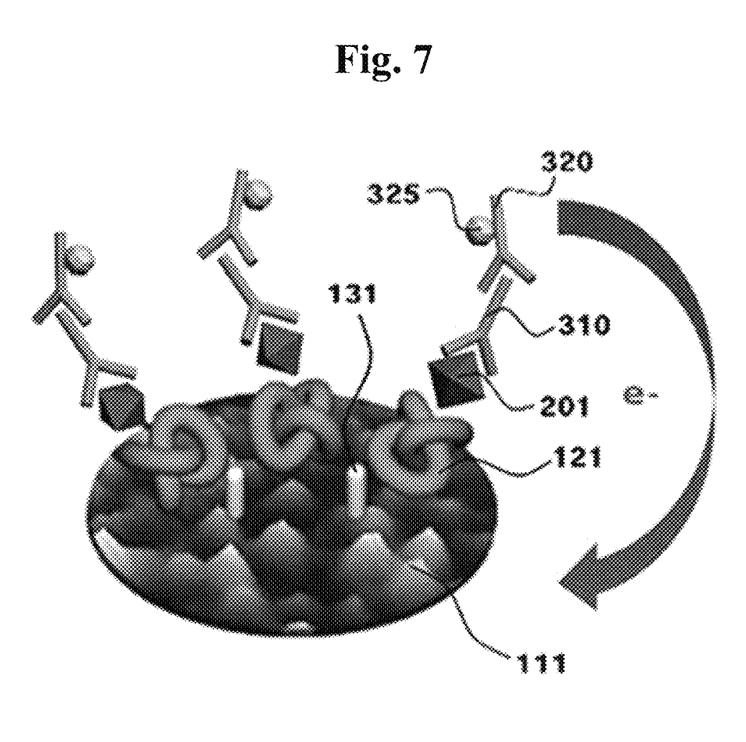
FIG. 7 is a schematic view illustrating the electrochemical sensing method using a norovirus detection sensor in accordance with the embodiment of the present invention.

FIGS. 5 to 7 show a schematic view illustrating an electrochemical sensing method using a norovirus detection sensor in accordance with one embodiment of the present invention.

Referring to FIG. 5, a bioreceptor included in the norovirus detection sensor employs concanavalin A 121 as a biological sample capture agent immobilized together with mercaptohexanol 121 on a substrate 111 composed of a three-dimensional gold nanosurface electrode, and is brought into contact with a norovirus sample to form a conjugate in which concanavalin A 121 is bound to norovirus 201.

Subsequently, as shown in FIG. 6, the conjugate may be labeled with a primary antibody 310 capable of selectively binding to norovirus 201 captured by concanavalin A 121. The primary antibody 310 may selectively recognize norovirus 201 attached to the conjugate, thereby forming an antigen-antibody interaction with norovirus 201.

Then, as shown in FIG. 7, the primary antibody 310 attached to norovirus 201 may be labeled with a secondary antibody 320 capable of recognizing the primary antibody 310 attached to norovirus 201 as an antigen. An electrochemical enzyme 325 is linked to the secondary antibody 320. As a result, norovirus 201 can be finally labeled, and an electrochemical signal can be generated by the electrochemical enzyme, whereby norovirus 201 can be sensed through detection of the electrochemical signal.

As such, the electrochemical sensing method using a norovirus detection sensor according to the present invention can reduce detection time by labeling norovirus captured in the norovirus detection sensor with high sensitivity and high selectivity with a detection antibody to which an electrochemical enzyme is linked.

In addition, the electrochemical sensing method using the norovirus detection sensor may have a limit of detection (LOD) ranging from 35 copies/mL to 60 copies/mL, and a detection selectivity for norovirus of 98% or more. Specifically, this will be described in the following Example and FIGS. 10 to 13.

A further aspect of the present invention provides an electrochemical sensing method using a norovirus detection sensor. Specifically, the electrochemical sensing method using the norovirus detection sensor employs a norovirus detection sensor including a bioreceptor and a signal detector, and includes 2-1) combining a norovirus sample including a ferricyanide solution with concanavalin A as a capture agent capable of binding to norovirus immobilized to a three-dimensional gold nanosurface electrode of the bioreceptor; and 2-2) measuring electrochemical signals generated by redox reaction of ferricyanide solution using the signal detector.

In step 2-1), a norovirus sample including a ferricyanide solution is combined with concanavalin A as a capture agent capable of binding to norovirus immobilized to the three-dimensional gold nanosurface electrode of the bioreceptor.

As described above, the bioreceptor included in the norovirus detection sensor employs the three-dimensional gold nanosurface electrode as a substrate, to which concanavalin A as a capture agent capable of capturing norovirus and binding to norovirus is immobilized. Additionally, mercaptohexanol is formed together with concanavalin A on the substrate.

The bioreceptor may be brought into contact with a norovirus sample including a ferricyanide solution to cause reaction. The ferricyanide solution is a self redox material, and receives or donates electrons on the electrode surface when voltage is applied to the three-dimensional gold nanosurface electrode as the substrate. As the bioreceptor is brought into contact with the ferricyanide solution having such characteristics as well as the norovirus sample, norovirus in the sample is captured by concanavalin A immobilized to the bioreceptor of the norovirus detection sensor, whereby the surface of the three-dimensional gold nanosurface electrode is covered, thereby decreasing the area in which the ferricyanide solution donates or receives electrons from the electrode. In other words, as the concentration of norovirus to be brought into contact with the bioreceptor and react with concanavalin A increases, the electrochemical signal from the ferricyanide solution can decrease. Accordingly, the intensity of the electrochemical signal generated by redox reaction of the ferricyanide solution can be changed according to the concentration of the norovirus sample.

In step 2-2), the electrochemical signal generated by redox reaction of the ferricyanide solution may be measured using the signal detector.

The signal detector measures the electrochemical signal generated by redox reaction of the ferricyanide solution generated in step 2-1), and may be a signal converter which senses the electrochemical signal and converts the signal into a physically measured value. As the signal converter for the signal detector, any device well-known in the art may be used.

The electrochemical sensing method using the ferricyanide solution according to the present invention will be described in detail with reference to FIG. 8. However, it should be understood that FIG. 8 shows merely an illustrative example and the present invention is not limited thereto FIG. 8 is a schematic view illustrating an electrochemical sensing method using a norovirus detection sensor in accordance with another embodiment of the present invention.

Figure 8:
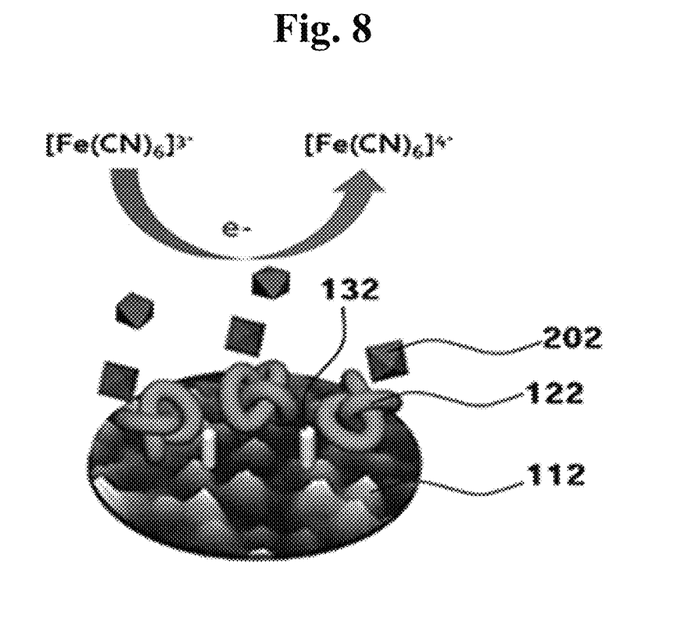
FIG. 8 is a schematic view illustrating an electrochemical sensing method using a norovirus detection sensor in accordance with another embodiment of the present invention.

Referring to FIG. 8, a bioreceptor included in the norovirus detection sensor employs concanavalin A 122 as a biological sample capture agent immobilized together with mercaptohexanol 122 on a substrate 112 composed of a three-dimensional gold nanosurface electrode, and is brought into contact with a norovirus sample to form a conjugate in which concanavalin A 121 is bound to norovirus 202. As the substrate 112 is covered with the conjugate, redox reaction of the ferricyanide solution can be declined. The concentration of norovirus 202 captured by concanavalin A 122 of the bioreceptor may be measured depending upon the degree of redox reaction of the ferricyanide solution.

As mentioned above, the electrochemical sensing method according to the present invention, in which the bioreceptor is brought into contact with the ferricyanide solution capable of generating an electrochemical signal through redox reaction with the three-dimensional gold nanosurface electrode as well as the norovirus sample, can measure the concentrations and presence of norovirus without separate labeling, and can perform high sensitivity sensing using the three-dimensional gold nanosurface electrode having high sensitivity.

As such, the present invention can enhance sensitivity of sensors by employing the three-dimensional gold nanosurface electrode having a wide surface area.

In addition, the present invention can have effects of reducing manufacturing costs using a non-antibody material, i.e., concanavalin A, which is inexpensive and readily available.

Further, the present invention can enhance selectivity of detecting norovirus using concanavalin A employed in the norovirus detection sensor.

Furthermore, the electrochemical sensing method using a ferricyanide solution can generate changes in electrochemical signals without separate labeling depending upon concentrations of norovirus, thereby reducing time for detection, which is actively utilized as a simple POCT (Point-of-care-test).

The present invention is not limited to specific effects as mentioned above, and a person having ordinary knowledge in the art could clearly understand other advantageous effects from the following description.

EXAMPLE

Example 1

Preparation of Norovirus Detection Sensor

Figure 9:
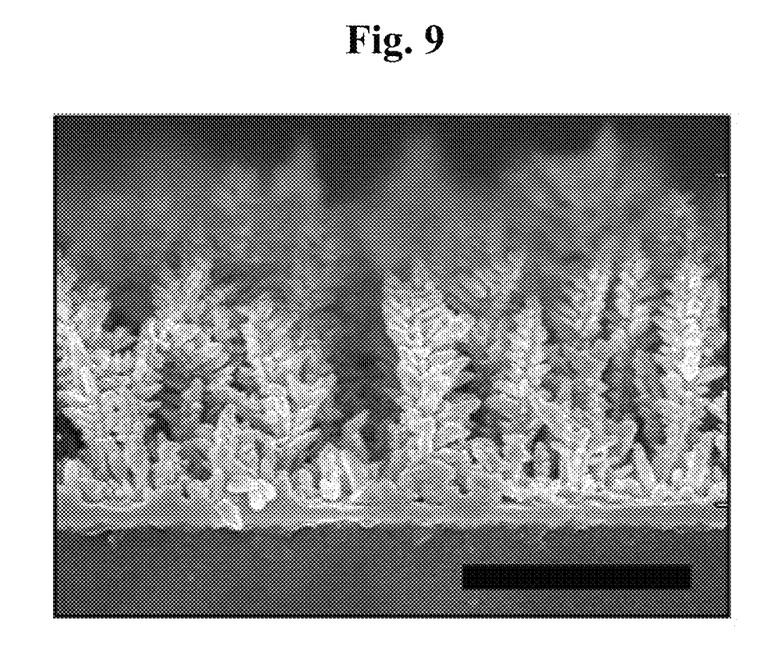
FIG. 9 is an SEM image of a three-dimensional gold nanosurface electrode prepared in Example 1.

A chromium (Cr) thin layer having a thickness of about 30 nm and a gold (Au) thin layer having a thickness of about 300 nm were sequentially formed on a glass substrate, followed by applying a photoresist (GXR-601) to form a pattern. After performing a lithography process, part of the gold (Au) thin layer and part of the chromium (Cr) thin layer on the glass substrate were removed using an etchant (Sigma Aldrich Co., Ltd.). The substrate was dipped in about 3 mg/ml of gold (III) chloride hydroxide dissolved in 0.5M sulfuric acid. Silver/silver chloride was used as a reference electrode, platinum (Pt) was used as a counter electrode, and the substrate was used as a work electrode. A voltage of −400 mV was applied for about 400 seconds to perform electrochemical deposition. As shown in FIG. 9, a gold electrode having a three-dimensional nanosurface structure was formed.

TBS as a buffer solution and 100 µg/mL of concanavalin A (Con A) were applied to the three-dimensional gold nanosurface electrode as a substrate by drop-casting at 4° C. for 1 hour. 1.0 mM/ml of mercaptohexanol was applied to the substrate, to which concanavalin A was immobilized, by drop casting at 25° C. for 2 hours, followed by washing with DI water.

Example 2

Electrochemical Sensing Method Using Detection Antibody

The three-dimensional gold nanosurface electrode to which concanavalin A was immobilized prepared in Example 1 was cultured at 4° C. such that norovirus had six concentrations ranging from $10^1$ copies/mL to $10^6$ copies/mL. In order to label a primary antibody, the electrode was dipped in 10 µl of milk containing approximately 10 µg/mL of a rabbit polyclonal anti-NoV antibody. Then, the electrode was dipped and cultured in about 1 µg/mL of an anti-rabbit IgG-ALP solution as a secondary antibody to which an electrochemical enzyme was linked. The resulting electrode was washed with a washing buffer solution (1× TBS and 0.05% Tween).

Experimental Example 1

Electrochemical Sensing Method (1) Using Detection Antibody

In order to detect norovirus, 10 mM of $MgCl_2$ including 20 mM of APP was supplied. In order to adjust pH to about 9.6, 50 mM of Tris-HCl as an electrochemical measuring solution was supplied while applying a voltage of −0.2V to +0.3V.

Figure 10:
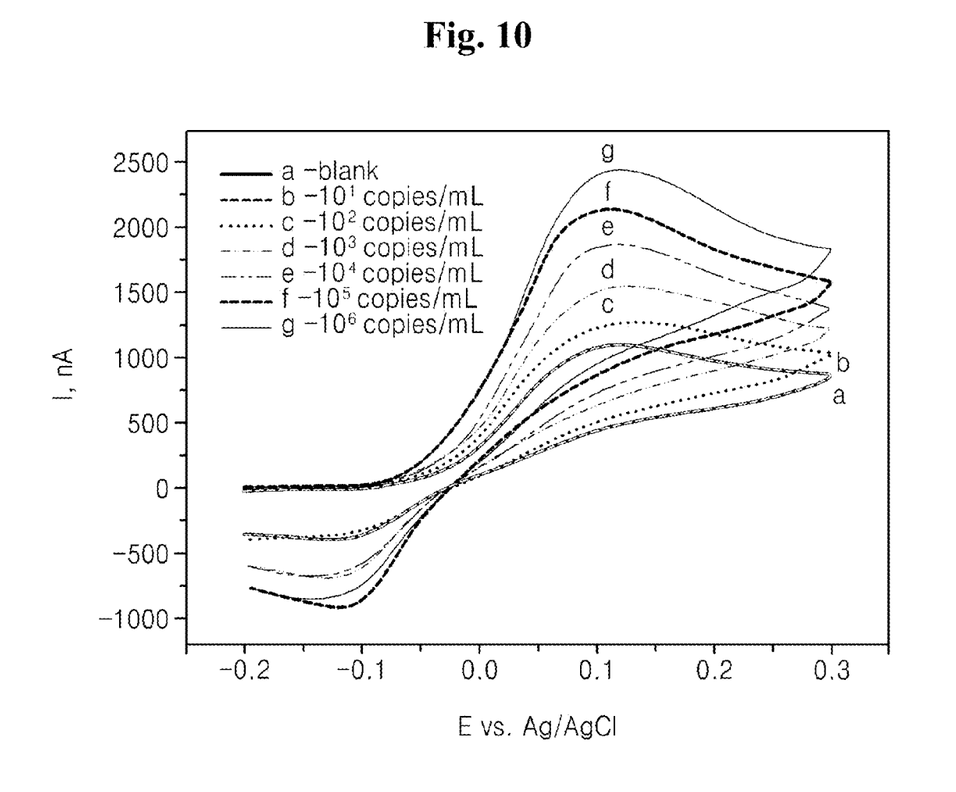
FIG. 10 is a graph depicting measured results of cyclic voltammetry depending upon concentrations of norovirus prepared in Example 2.
Figure 11:
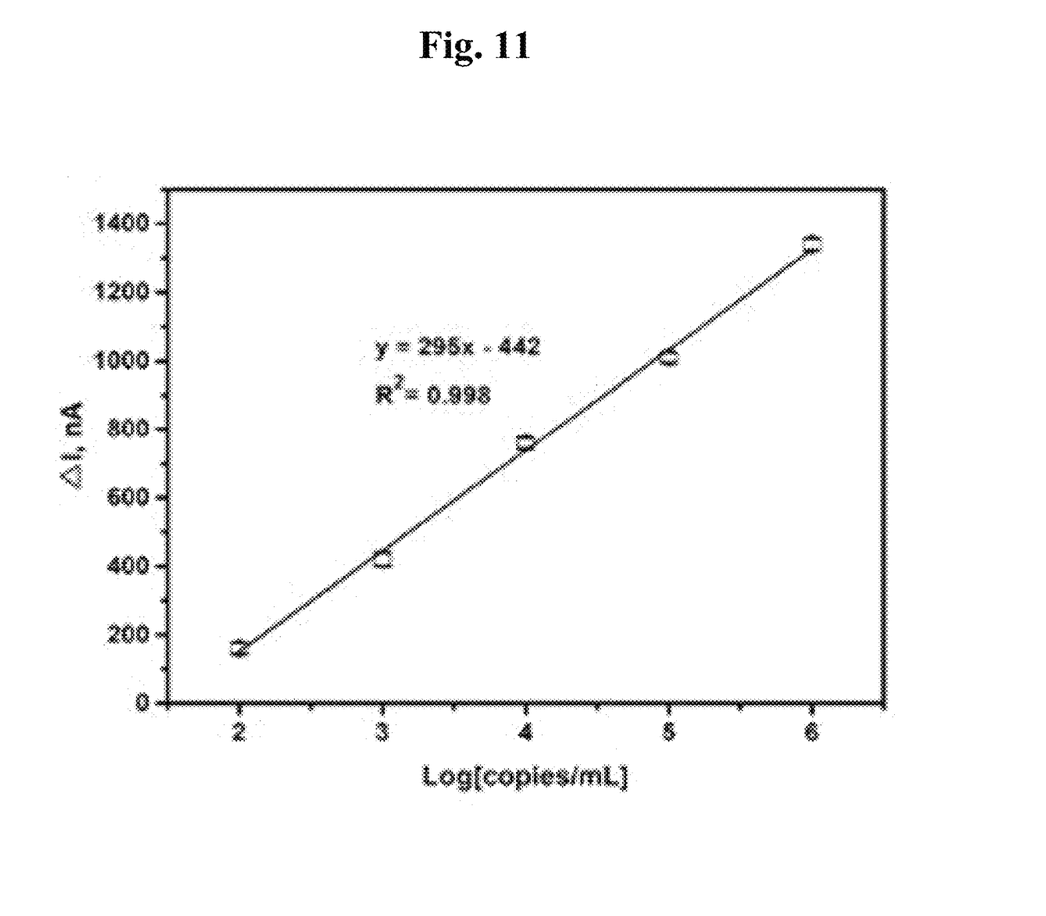
FIG. 11 is a calibration curve obtained using electrochemical signals at a redox potential of 0.1V depending upon concentrations of norovirus prepared in Example 2.

FIGS. 10 and 11 are a graph depicting measured results of cyclic voltammetry depending upon concentrations of norovirus prepared in Example 2 and a calibration curve using electrochemical signals at a redox potential of 0.1V, respectively.

Referring to FIG. 10, in the measured results of cyclic voltammetry, increase in current curves indicates increase in electrochemical enzyme (ALP) immobilized to norovirus, from which concentrations of norovirus can be measured. Specifically, as the concentration of norovirus increases from $10^2$ copies/mL to $10^6$ copies/mL, voltage-current curves become distinct, which indicates increase in current intensity.

Referring to FIG. 11, it can be seen that, as the concentration of norovirus increases from $10^2$ copies/mL to $10^6$ copies/mL, the changes in current measured at a redox potential of 0.1V are linear. In addition, it can be seen from the measured value that the norovirus detection sensor according to the present invention has a limit of detection of 35 copies/mL. Specifically, the limit of detection can be calculated in accordance with Equation 1:

$$y=3*(x/a) \tag{1},$$

wherein y is a limit of detection, x is a standard deviation for current values at blank, and a is a slope of the linear curve depicting a current value at blank and current values at concentrations different from blank.

Accordingly, the limit of detection of the norovirus detection sensor according to Experimental Example 1 measured by Equation 1 is 3*(12.95/1.1), which can be converted to 35 copies/mL.

Experimental Example 2

Electrochemical Sensing Method (2) Using Detection Antibody

In order to evaluate norovirus selective detection capability, norovirus having a concentration of $10^3$ copies/mL, hepatitis virus A (HAV) having a concentration of $10^3$ copies/mL and hepatitis virus E (HEV) having a concentration of $10^3$ copies/mL were mixed and sensed.

Figure 12:
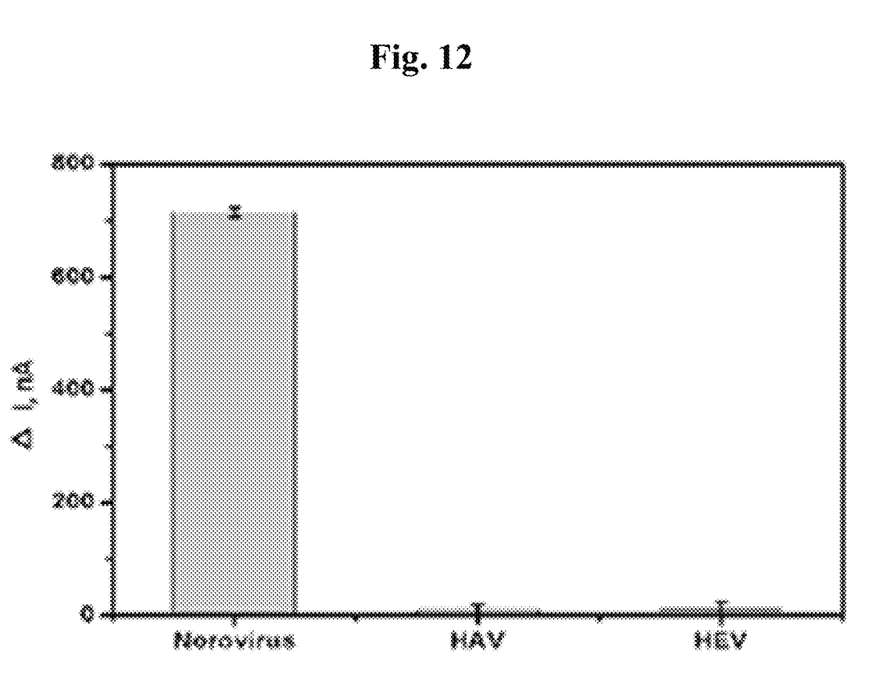
FIG. 12 shows results of selectivity tests of the electrochemical sensing method using a norovirus detection sensor measured in Experimental Example 2.

FIG. 12 shows results of selectivity testing of the electrochemical sensing method using a norovirus detection sensor measured in Experimental Example 2.

Referring to FIG. 12, it can be seen that the norovirus detection sensor according to the present invention detects norovirus at a selectivity of 98% as compared with other viruses. The norovirus detection sensor according to the present invention can exhibit high selectivity through a simplified sensor device by disposing concanavalin A on the three-dimensional gold nanosurface electrode having a wide surface area.

Experimental Example 3

Electrochemical Sensing Method (3) Using Detection Antibody 10 g of lettuce was homogenized in 50 mL of Tris elution buffer at room temperature using a Stomacher LB-400 (Sibata Co., Ltd.) for 15 minutes. Then, the resulting solution was centrifuged, thereby collecting a supernatant. Norovirus samples were prepared such that the samples had a concentration of $10^1$ copies/mL, $10^2$ copies/mL, $10^3$ copies/mL, $10^4$ copies/mL, $10^5$ copies/mL, and $10^6$ copies/mL, and no norovirus. The norovirus and lettuce extract were mixed and subjected to sensing.

Figure 13:
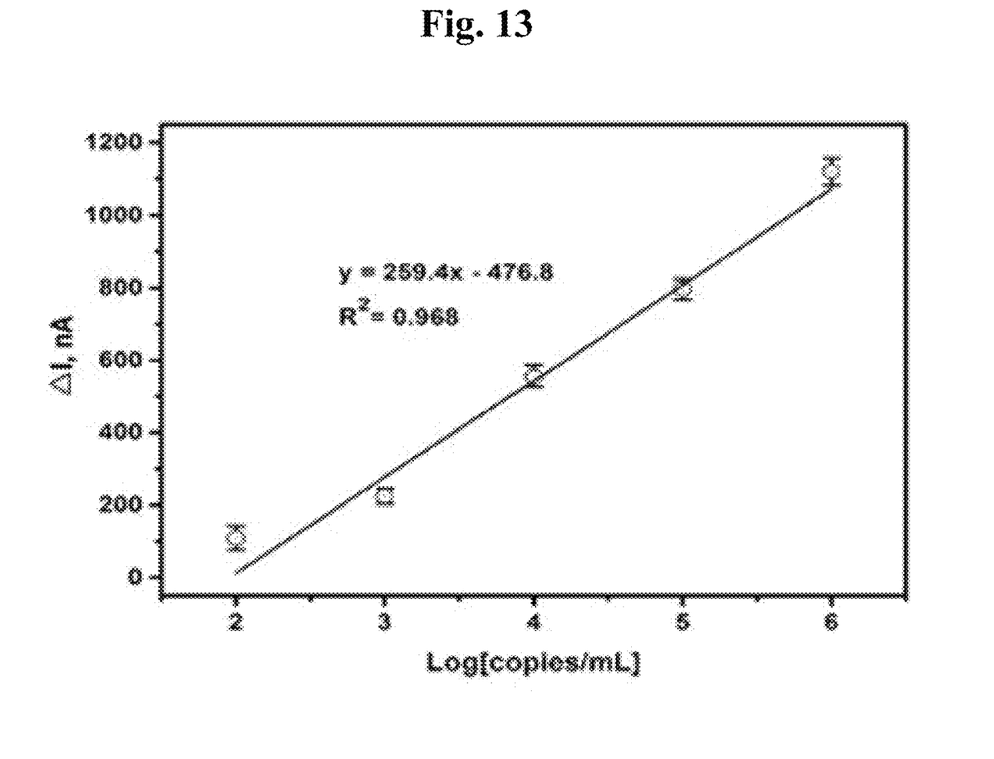
FIG. 13 is a calibration curve obtained using electrochemical signals at a redox potential of 0.1V depending upon concentrations of norovirus in Experimental Example 3.

FIG. 13 is a calibration curve obtained using electrochemical signals at a redox potential of 0.1V depending upon concentrations of norovirus prepared in Experimental Example 3.

Referring to FIG. 13, it can be confirmed that, as the concentration of norovirus increases from $10^2$ copies/mL to $10^6$ copies/mL, changes in current measured at a redox potential of 0.1V are linear. In addition, the measured value representing the linear curve may be calculated through Equation 1. The limit of detection of the norovirus detection sensor according to the present invention is 3*(21.89/1.09), which can be converted to 60 copies/mL.

This value is slightly higher than that in pure sample having no other foreign substance and is less than $10^2$ copies/mL, which is a value indicating infection of norovirus. It can be confirmed that the norovirus detection sensor according to the present invention and electrochemical sensing method employing the sensor can easily detect norovirus in an actual food extract solution.

Example 3

Electrochemical Sensing Method Using Ferricyanide Solution

The three-dimensional gold nanosurface electrode prepared in Example 1, to which concanavalin A was immobilized, was cultured at 4° C. in a sample having no norovirus and a sample having a concentration of norovirus of $10^3$ copies/mL, followed by mixing with a ferricyanide solution.

Figure 14:
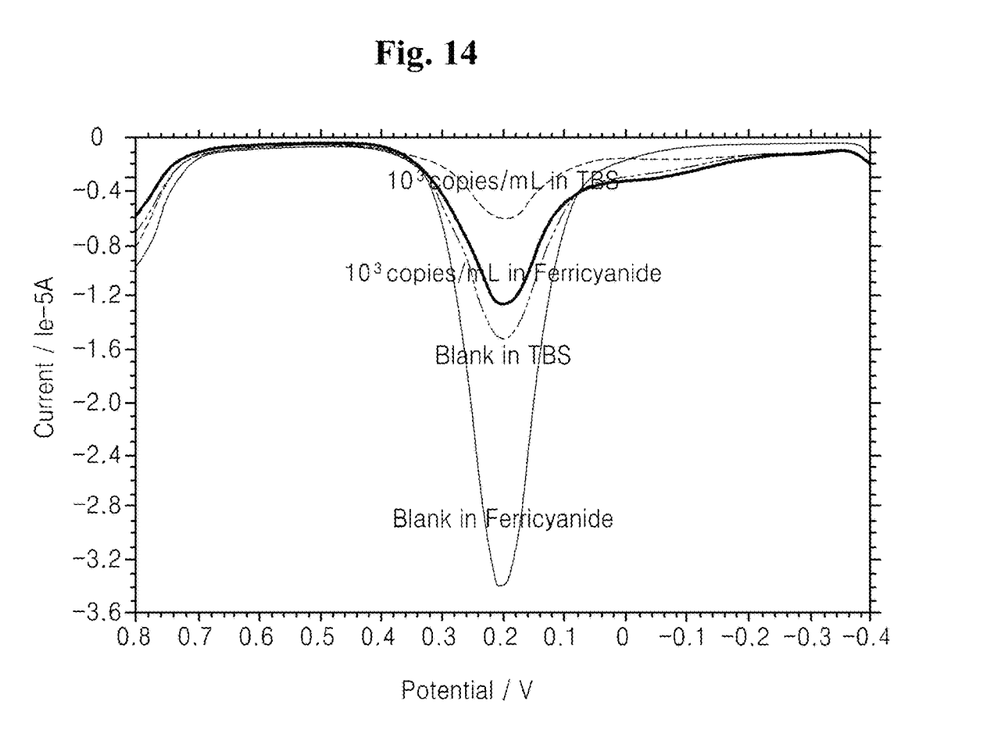
FIG. 14 is a graph depicting results of measuring voltage-current change in Example 3.

FIG. 14 is a graph depicting measured results of voltage-current change in Example 3.

Referring to FIG. 14, it can be seen that there is a significant difference in measured values of voltage-current between a sample having no norovirus and a sample having a concentration of $10^3$ copies/mL at 0.2 V. This means that an electrochemical signal of the ferricyanide solution decreases depending upon the presence of norovirus. As the concentration of norovirus increases, the three-dimensional gold nanosurface electrode used as a substrate is covered with norovirus captured by concanavalin A immobilized to the three-dimensional gold nanosurface electrode, which in turn decreases redox reaction of the ferricyanide solution.

The electrochemical sensing method using the ferricyanide solution can generate electrochemical signals according to concentrations of norovirus without separate labeling, which decreases detection time.

Although the present invention has been described with reference to some embodiments, it should be understood that the foregoing embodiments are provided for illustration only and are not to be construed in any way as limiting the present invention, and that various modifications, changes, alterations, and equivalent embodiments can be made by those skilled in the art without departing from the spirit and scope of the invention.

LIST OF REFERENCE NUMERALS

100: Bioreceptor
110, 111, 112: Substrate
120, 121, 122: Concanavalin A
130, 131, 132: Mercaptohexanol
200, 201, 202: Norovirus
300: Signal detector
310: Primary antibody
320: Secondary antibody
325: Electrochemical enzyme

What is claimed is:
1. A norovirus detection sensor comprising:
a bioreceptor; and a signal detector,
wherein
   the surface of bioreceptor comprises a three-dimensional gold nanosurface electrode substrate,
   the three-dimensional gold nanosurface electrode substrate is covered with
      a protein having a specific binding property with the norovirus and
      a mercaptohexanol preventing non-specific binding to the substrate,
   the protein is concanavalin A immobilized on the three-dimensional gold nanosurface electrode substrate as a sample capture agent for causing the concanavalin A to bind to the norovirus, and
   the mercaptohexanol is formed, by drop-casting, in an exposed area of the three-dimensional gold nanosurface electrode substrate in which the concanavalin A is not immobilized to serve to cover the exposed are,
   the signal detector detects electrochemical signal generated from the bioreceptor, and qualitatively and quantitatively calculates, from the detected electrochemical signal, values of the biological sample, and
   the norovirus detection sensor has a limit of detection (LOD) ranging from 35 copies/mL to 60 copies/mL and a detection selectivity for norovirus of 98% or more.

2. The norovirus detection sensor according to claim 1, wherein the three-dimensional gold nanosurface electrode substrate is formed through an electrochemical deposition process.

* * * * *